United States Patent [19]
Magliochetti et al.

[11] Patent Number: 5,729,653
[45] Date of Patent: Mar. 17, 1998

[54] FLUID WARMING SYSTEM

[75] Inventors: Michael J. Magliochetti; Carolyn Pals, both of Iowa City, Iowa

[73] Assignee: Urosurge, Inc., Coralville, Iowa

[21] Appl. No.: 487,852

[22] Filed: Jun. 7, 1995

[51] Int. Cl.$^6$ .................. H05B 3/78; H05B 1/02; F24H 1/10

[52] U.S. Cl. .................. 392/485; 392/487; 392/491; 392/493; 219/497

[58] Field of Search .................. 392/485, 491, 392/494, 470, 471, 478, 449, 451, 455, 479, 493, 486; 219/544, 546, 484, 50 Z, 497, 506, 442, 492; 128/200.18; 73/290 R

[56] References Cited

U.S. PATENT DOCUMENTS

| | | |
|---|---|---|
| Re. 26,828 | 3/1970 | Atkins et al. .................. 73/290 R |
| 1,987,119 | 1/1935 | Long .................. 219/39 |
| 3,485,245 | 12/1969 | Lahr et al. .................. 128/272 |
| 4,038,519 | 7/1977 | Foucras .................. 219/301 |
| 4,084,587 | 4/1978 | Lindsey .................. 128/200.18 |
| 4,167,663 | 9/1979 | Granzow, Jr. et al. .................. 392/470 |
| 4,185,187 | 1/1980 | Rogers .................. 392/451 |
| 4,314,143 | 2/1982 | Bilstad et al. .................. 392/470 |
| 4,404,462 | 9/1983 | Murray .................. 219/502 |
| 4,532,414 | 7/1985 | Shah et al. .................. 219/308 |
| 4,680,445 | 7/1987 | Ogawa .................. 219/299 |
| 4,707,587 | 11/1987 | Greenblatt .................. 392/470 |
| 4,844,072 | 7/1989 | French et al. .................. 392/470 |
| 4,847,470 | 7/1989 | Bakke .................. 219/299 |
| 4,906,816 | 3/1990 | van Leerdam .................. 219/299 |
| 5,108,372 | 4/1992 | Swenson .................. 604/113 |
| 5,211,631 | 5/1993 | Sheaff .................. 604/113 |
| 5,212,763 | 5/1993 | Arold et al. .................. 219/502 |
| 5,216,743 | 6/1993 | Seitz .................. 392/486 |
| 5,325,822 | 7/1994 | Fernandez .................. 392/451 |
| 5,438,642 | 8/1995 | Posen .................. 392/485 |

FOREIGN PATENT DOCUMENTS

| | | |
|---|---|---|
| 2505294 | 11/1982 | France . |
| 4030368 | 11/1991 | Germany . |
| 9201792 | 5/1992 | Germany . |
| 198839 | 10/1938 | Switzerland . |
| 1161366 | 8/1969 | United Kingdom . |
| WO 92/17040 | 10/1992 | WIPO . |

*Primary Examiner*—Tu B. Hoang
*Attorney, Agent, or Firm*—Thomas J. Engellenner; Mark D. Russett; Lahive & Cockfield, LLP

[57] ABSTRACT

Devices and methods for heating a fluid to normothermic temperature prior to delivery of the fluid to a patient are disclosed. In one embodiment, a fluid to be warmed prior to delivery to a patient can be passed through a polymeric, flow-through chamber disposed in the fluid delivery line. An electrically resistive heating element for heating the fluid can be molded into the chamber to heat the fluid from room or ambient storage temperatures to a normothermic or body temperature of the patient. A probe of a temperature monitoring element can be used to monitor the temperature of the fluid exiting the chamber. In another embodiment, this information can be relayed back to a controller for controlling the power to the resistance element and hence, the temperature of the fluid. In still another embodiment, an infrared temperature sensor can be used for monitoring the temperature on the fluid exiting the chamber by scanning through a window in the outlet port of the chamber or elsewhere in the fluid line.

26 Claims, 6 Drawing Sheets

FLUID WARMING SYSTEM

BACKGROUND OF THE INVENTION

The field of this invention concerns heating fluids and, in particular, heating fluids for delivery to a patient.

One of the problems typically encountered in heating transfusion, infusion or irrigation fluids for delivery to a patient is that such fluids are typically stored at room temperature, which is much lower than a patient's body temperature. Introduction of cold fluids into a patient may well cause discomfort, shock, or another type of trauma. Storage of quantities of warmed fluids, however, is potentially unnecessarily expensive in terms of the energy costs. In addition, the temperature control involved in the storage of warmed fluids is problematic, because the temperature of such fluids still must be maintained while the fluids are transported from the storage area and delivered to the patients.

Various techniques have been used for heating a fluid in-line prior to delivery to a patient. Electrical resistive heating has been used to heat transfusion fluids, in particular. See, for example, U.S. Pat. Nos. 4,906,816 by Van Leerdam; 4,847,470 by Bakke; and 4,532,414 by Shah et al. Typically, a bag or a conduit containing a fluid to be warmed may be placed inside an enclosure. Heating plates contained inside the enclosure may be pressed or clamped against the fluid container. Electrical current is supplied to the heating plates, such that the plates warm the fluid container. When the desired heating is accomplished, the fluid container may be released or removed from the enclosure, and the warmed fluid may be delivered to the body.

Such devices can be cumbersome and awkward, however, because they require that an operator place the fluid container inside the enclosure, clamp or press the heating plates against the fluid container, and subsequently remove the fluid container before the fluid may be delivered to the body. In addition, the temperature monitoring of such devices may be limited, because they typically only measure the temperature of the fluid containers and/or heating elements.

Accordingly, there exists a need for devices and methods for heating fluids, particularly for transfusion and/or irrigation purposes.

SUMMARY OF THE INVENTION

Devices and methods are disclosed for heating a fluid to normothermic temperatures prior to the delivery of the fluid to a patient. The present invention is based on the recognition that an electrically resistive heating element can be molded into a flow-through chamber, and this chamber can be inserted in a flow-line for warming fluids to normothermic temperatures prior to the delivery of such fluids to a body. The term "normothermic temperatures", as used herein, encompasses equilibrium body temperatures in the range of about 34° C. to 45° C.

In one embodiment of the invention, a fluid to be warmed prior to delivery to a patient can be passed through a flow-through polymeric chamber disposed in the delivery fluid flow line. An electrically resistive heating element for heating the fluid is molded into the chamber. A temperature monitoring element, such as a thermistor, can be used to monitor the temperature of the fluid. The thermistor probe can be inserted directly into the fluid stream exiting the chamber to measure the outlet fluid temperature.

The chamber can consist of a disposable shell with a capacity for a fluid flow ranging from about 10 ml/min to about 1000 ml/min. The fluid can flow by gravity or mechanical means into the chamber. The heating element can be inserted into a center wall in the chamber such that fluid can flow on both sides of the heating element for maximum heating efficiency. Alternatively, the heating element can be inserted into one or both of the chamber side walls. A biocompatible protective layer can be disposed between the heating element and the fluid. A flexible insulating material can also be disposed to surround a portion of the heating element or the chamber to reduce heat losses. The chamber can contain baffles for providing a restricted labyrinth flow path for optimizing heating uniformity (e.g., by creating a turbulent flow stream). Alternatively, the chamber can provide a completely unrestricted flow path or can contain baffles for providing an unrestricted labyrinth flow path. Flexible tubing can be used to deliver the fluid to and from the chamber for increased ease and flexibility.

The electrically resistive heating element can include, but is not limited to, an etched metal foil, a carbon dispersion resistor or a dye-cut resistor. The heating element can have a capacity of at least about 50 Watts. In one aspect of the invention, the heating element can heat the fluid a maximum of about 50° C. above the fluid's storage temperature.

In another aspect of the invention, a system including a flow-through polymeric chamber and an electrically resistive heating element, and further including an external controller can be used to warm a fluid prior to delivery to a patient. The controller can control the power supplied to the heating element through an electrical connection element having pads or other electrical connections disposed on the chamber. The system can also include an attachment mechanism for attaching the controller to the chamber to receive this electrical connection element. In addition, the system can include a mounting mechanism for mounting the controller to a support pole.

In yet another aspect of the invention, the temperature of the fluid can be monitored during operation of the system. In one embodiment, a temperature sensor can be deployed in the fluid flow path. Alternatively, the temperature of the heating element can be monitored. For example, the electrical resistance of the heating circuit can be monitored and used to calculate indirectly the temperature of the heating element and, hence, the fluid.

The temperature monitoring element and/or the resistance sensor can be integrated into the chamber, but physically separate from the heating element. Alternatively, the temperature monitoring element and/or the resistance sensor can be integrated onto the controller.

The system can be equipped with a number of operational safety and control features to provide for safe and easy operation of the invention. The system can have a power shut-off circuit loop for automatically shutting off power and/or an alarm for sounding when a fault condition occurs. Fault conditions can include the outlet temperature of the fluid, the resistance of the heating element and/or the fluid resistance exceeding a predetermined limit. Further, additional temperature monitoring and control can be accomplished with an infrared temperature sensor disposed on the controller which senses outlet fluid temperature through a window on the chamber outlet or elsewhere in the fluid line. The system can also be equipped with a LED two-digital display of the outlet fluid temperature for easy visual temperature monitoring. In addition, the system can be equipped with one or more lights for indicating whether the desired pre-determined outlet fluid temperature has been reached.

Because of the simplicity and safety of the present invention's operation and its precise measurement of fluid temperature, the present invention represents a valuable addition to the art of biological fluid warming, and in particular, the art of irrigation fluid warming.

DETAILED DESCRIPTION OF THE INVENTION

Figure 1A:
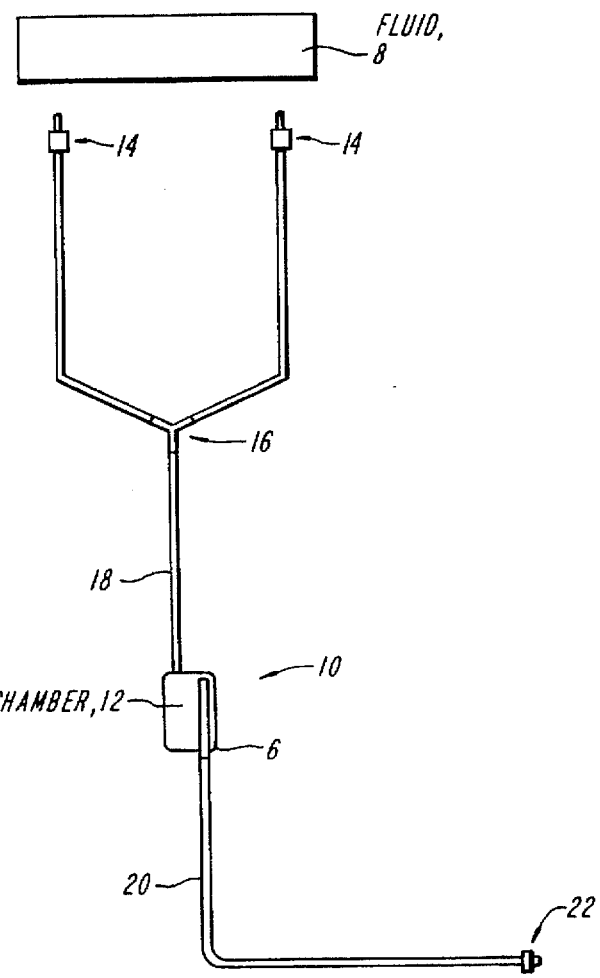
FIG. 1A is a perspective view of the flow-through chamber of the present invention disposed in a gravity-fed fluid delivery line.
Figure 1B:
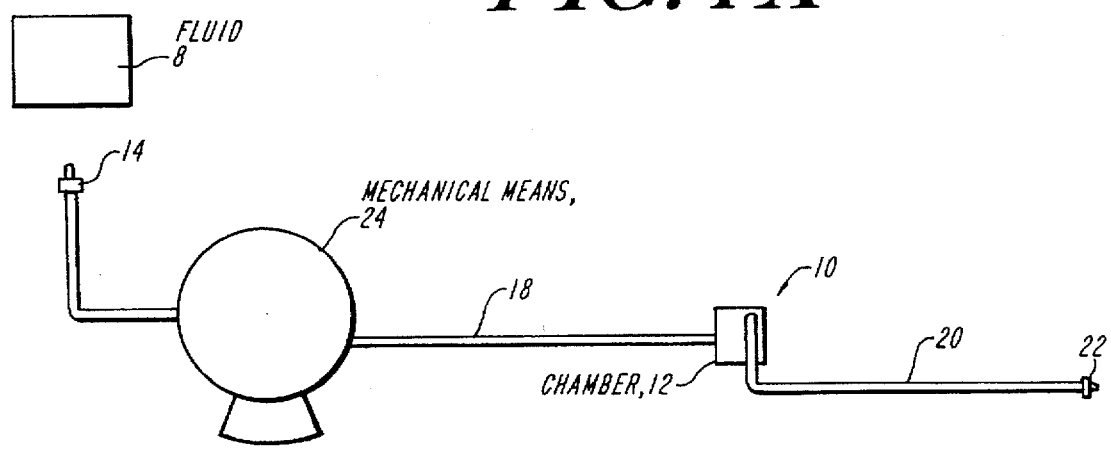
FIG. 1B is a perspective view of the flow-through chamber of the present invention disposed in a mechanically-fed fluid delivery line.

The present invention provides an electrically resistive heating element molded into a flow-through polymeric chamber for warming fluids in-line to normothermic temperatures prior to delivery to a patient. FIG. 1A illustrates a perspective view of the device 10 of the present invention having a chamber 12 disposed in association with a source of fluid 8 and a fluid delivery line consisting of two IV bag spikes 14, a Y connector 16, a gravity-fed fluid line 18 entering the chamber 12, a fluid line 20 exiting the chamber, and a luer connector 22 for connecting the fluid line 20 to a device such as irrigator or IV line for delivering the fluid 8 into a patient. Alternatively, the fluid entering the device can be delivered by mechanical means 24, as shown in FIG. 1B.

Figure 2A:
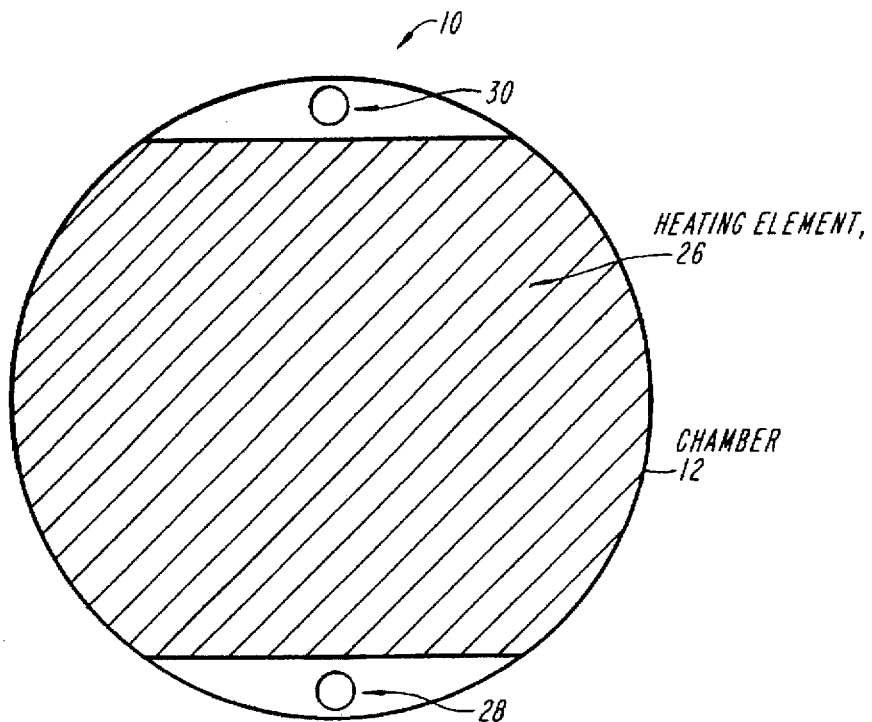
FIG. 2A is an inside view of a disk-shaped flow-through chamber.
Figure 2B:
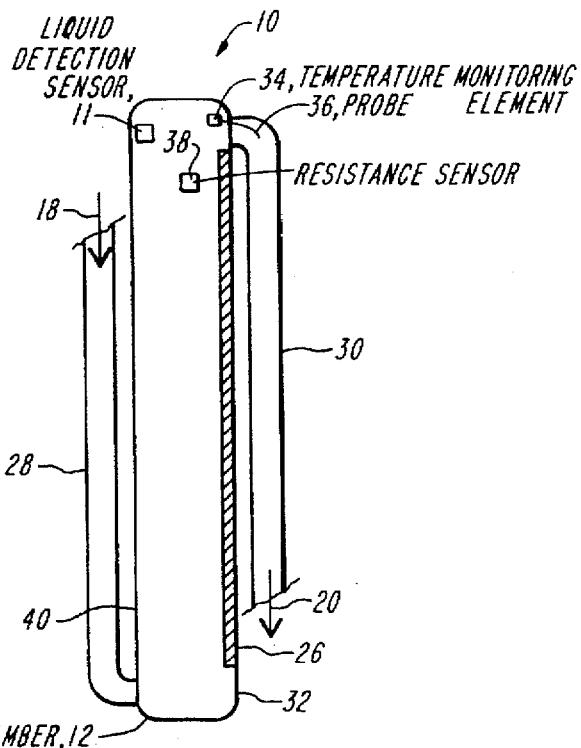
FIG. 2B is an inside side view of a flow-through chamber showing the heating element disposed on a side wall of the chamber.

FIG. 2A illustrates an inside frontal view of a chamber 12 having an electrically resistive heating element 26, an inlet port 28 and an outlet port 30. The fluid inlet port 28 directs the fluid to the bottom of the chamber and the fluid outlet port 30 allows the fluid to exit from the top of the chamber to facilitate air escape during priming of the chamber. FIG. 2B, which is an inside side view of the chamber 12, shows the electrically resistive heating element 26 disposed on a side wall 32 of the chamber 12 such that the fluid flows along one side of this element 26. A temperature monitoring element 34, such as a thermistor or a thermocouple, can be used to monitor the temperature of the fluid 20 exiting outlet port 30. A probe 36 of the temperature monitoring element 34 can be inserted directly into the fluid line 20 exiting the chamber to measure the outlet fluid temperature. A resistance sensor 38 can be integrated into the chamber 12 but physically separate from the heating element to measure the fluid temperature. A liquid detection sensor 11 can also be employed to measure the resistance of the fluid in the chamber.

The chamber 12 can consist of a disposable shell with a capacity for a fluid flow ranging from about 10 ml/min to about 1000 ml/min. The chamber 12 can be manufactured through any number of known techniques, such as injection molding with any FDA approved medical grade thermoplastic (e.g. polypropylene, polyethylene, nylon or PVC). The chamber can also be made of different shapes, and the rectangular and disk shapes shown in FIGS. 1A and 2A, respectively, are illustrated for exemplary purposes only.

Figure 3:
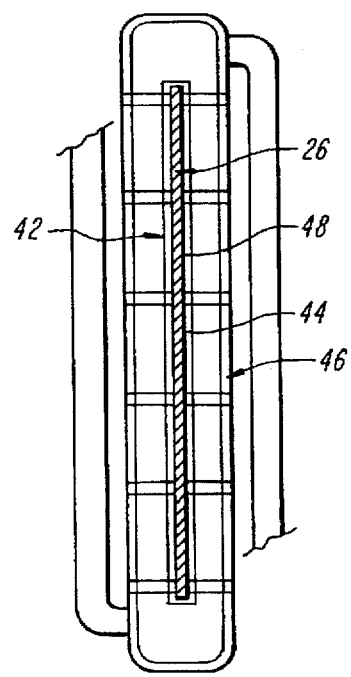
FIG. 3 is an inside view of a flow-through chamber with a heating element disposed on the center wall of the chamber.

Although FIG. 2A shows the heating element 26 inserted into a chamber sidewall 32, the heating element 26 can also be inserted into either (or both) of the chamber side walls 32 and 40. Alternatively, FIG. 3 shows that the heating element 26 can be inserted into a center wall 42 of the chamber 12 such that fluid can flow on both sides of the heating element 26 for maximum heating efficiency. The heating element 26 can be contained between two layers 48 of a laminate material, such as polyimides or polyesters, that will have thermal properties such that they will not melt or otherwise degrade at the temperature of heater operation. In addition, FIG. 3 illustrates that a biocompatible protective layer 44, which does not further hinder the heat transfer to the fluid, can be disposed between at least one portion of the heating element and the fluid. Again, this layer can be made of any biocompatible material with high thermal conductivity (e.g. polypropylene, polyethylene, nylon or PVC). This layer can be applied to the heating element by a plasma coating process. FIG. 3 also illustrates that an insulating material 46 can be disposed to surround at least a portion of the outer surface of the heating element 26 or the chamber to reduce heat losses.

Figure 4:
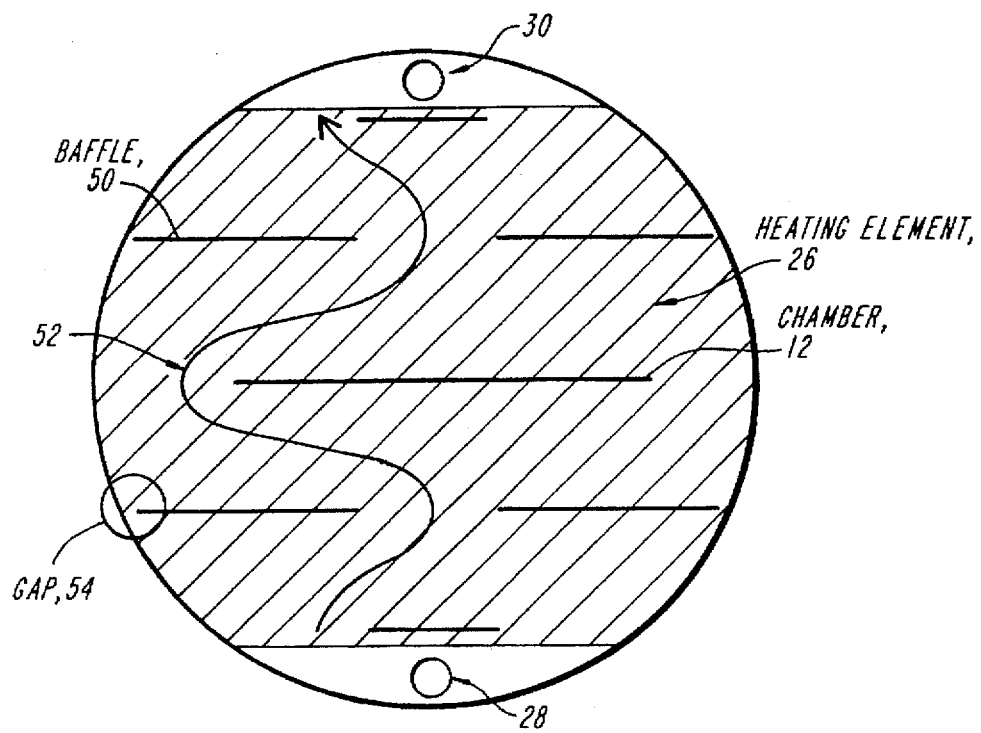
FIG. 4 is an inside view of a disk-shaped flow-through chamber with horizontal baffles for an unrestricted labyrinth flow path.
Figure 5:
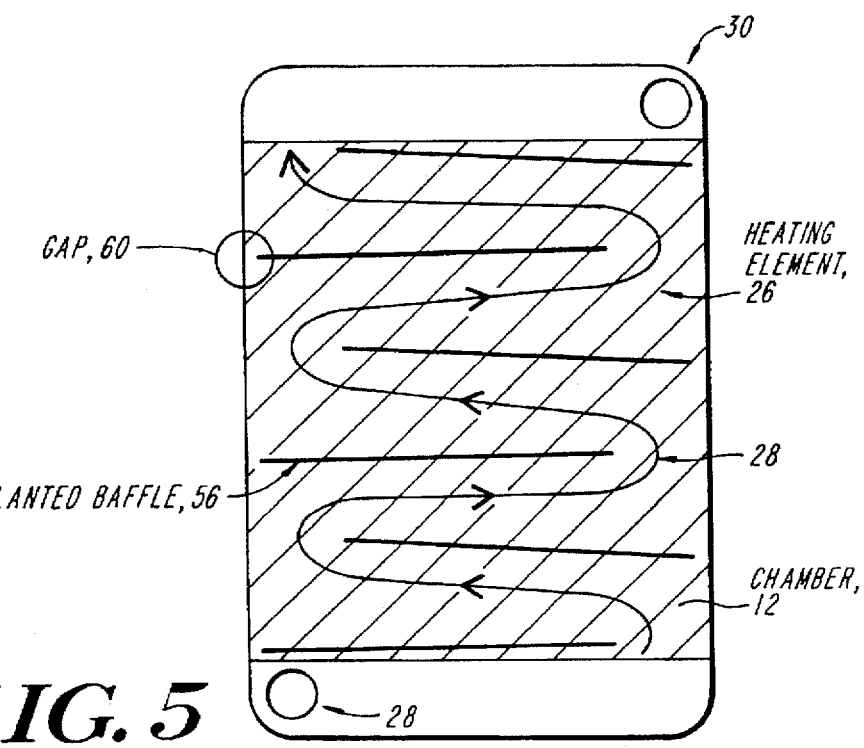
FIG. 5 is an inside view of a rectangular flow-through chamber with slanted baffles for a restricted labyrinth flow path.

FIG. 4 shows that horizontal baffles 50 may be inserted into the chamber 12 to form an unrestricted labyrinth flow path 52. The unrestricted labyrinth flow path 52 does not allow the fluid to flow straight through the chamber 12, but at the same time, does not restrict the flow to a single defined flow path. Gaps 54 between the baffles and the chamber walls eliminate fluid dead spots or eddies that would normally occur when the flowing fluid is forced around a corner. FIG. 5 shows the chamber 12 with slanted baffles 56 forming a restricted labyrinth flow path 58. In a restricted labyrinth flow path 58, slanted baffles 56 force the fluid to flow in a defined labyrinth path. As in the unrestricted labyrinth flow path, the gaps 60 between the slanted baffles 56 and the walls of the chamber eliminate the fluid dead spots or eddies that normally occur when flowing fluid is forced around a corner. In addition, the slanted baffles 56 facilitate the escape of air during the priming process.

Figure 6:
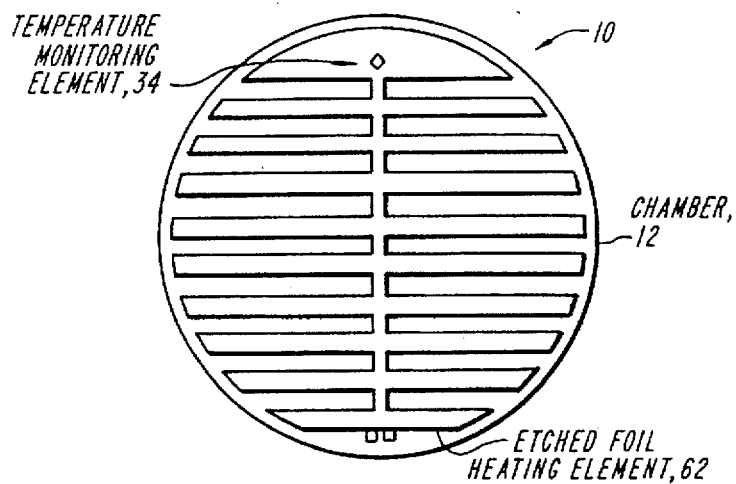
FIG. 6 shows an etched metal foil resistor for use as a heating element in accordance with the invention.
Figure 7:
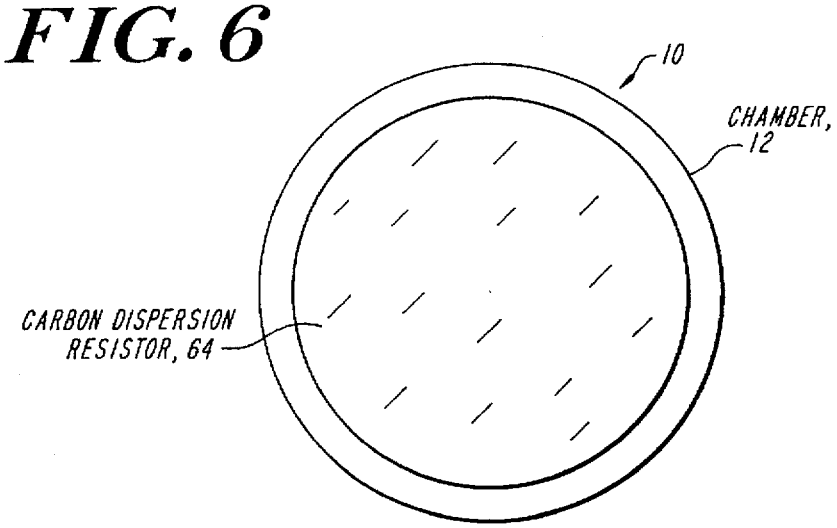
FIG. 7 shows a carbon dispersion resistor for use as a heating element in accordance with the invention.
Figure 8:
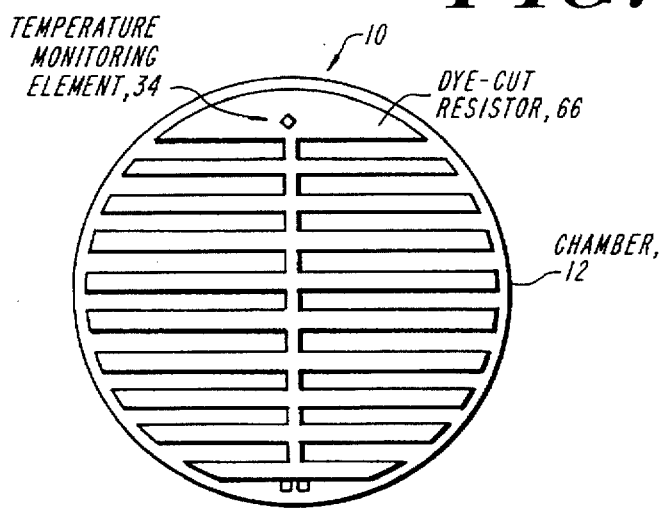
FIG. 8 shows a dye-cut resistor for use as a heating element in accordance with the invention.

The electrically resistive heating element 26 is made up of a conductor which heats up in response to an applied electric current. This heating element 26 can include, but is not limited, to an etched metal foil 62, as shown in FIG. 6, a carbon dispersion resistor 64, as shown in FIG. 7, or a dye-cut resistor 66, as shown in FIG. 8. The heating element can have a capacity of at least about 50 Watts. This power requirement can be accomplished with a variety of resistance/voltage/current configurations. The area of the heating element can be about 15 cm$^2$ to about 600 cm$^2$. In one aspect of the invention, the heating element can heat the fluid a maximum of about 50° C. above the storage temperature of the fluid.

Figure 9:
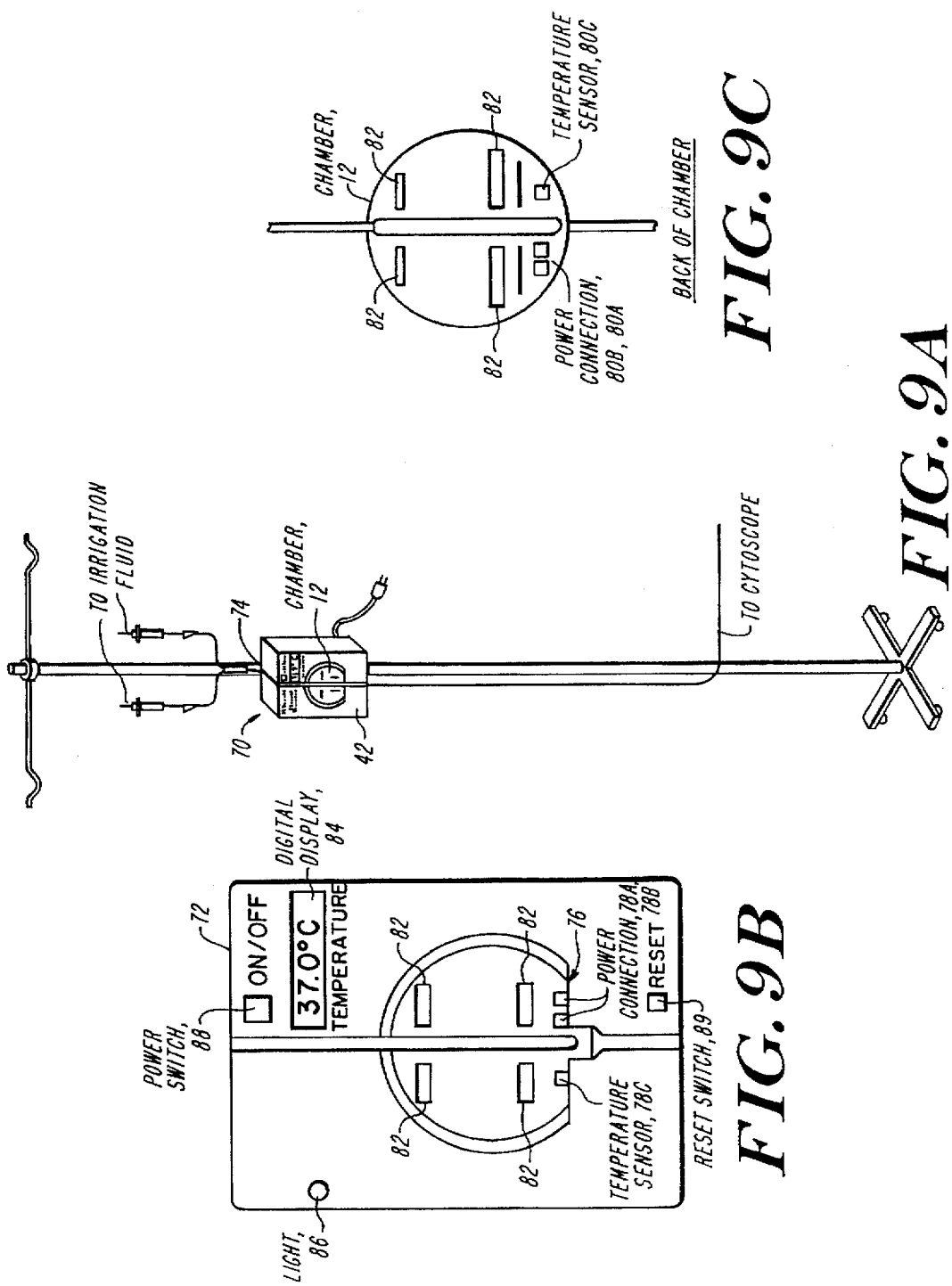
FIG. 9A is an outside view of the system of the present invention mounted on a vertical support pole.
FIG. 9B is an outside front view of the controller of the system of the present invention.
FIG. 9C is an outside front view of a disk-shaped flow-through chamber.

The present invention also provides a system including a flow-through polymeric chamber, an electrically resistive heating element, and an external controller for heating fluids prior to delivery to a patient. FIG. 9A shows an outside view of this system 70 with the chamber 12 attached to the controller 72, which, in turn, is mounted to a vertical support pole with a mounting mechanism 74. The controller 72 can monitor the temperature of the outlet fluid and control the power supply to the heating element through an electrical connection element 76 having pads 78A, 78B, & 78C disposed on the front of the controller, shown in FIG. 9B, and pads 80A, 80B, & 80C disposed on the back of the chamber, as shown in FIG. 9C. Alternatively, other electrical connections such as prongs, jacks, plugs or the like can be used. All electrical connections can be safety interlocked to the proper installation of the disposable. The attachment mechanism 82 for attaching the front of the controller 72 to back of the chamber 12 to receive this electrical connection element is also shown in FIGS. 9B and 9C.

FIG. 9B further illustrates that the front of the controller 72 can be equipped with a LED two-digital display 84 of the outlet fluid temperature for easy visual temperature monitoring. In addition, the front of the controller 72 can be equipped with one or more lights 86 for indicating a fault condition and/or whether the desired pre-determined outlet fluid temperature has been reached, a power ON/OFF switch 88 and a RESET switch 89 for easy operator access. The controller 72 can be AC line powered and switchable to operate at either 110 Vac or 220 Vac line voltage. The AC input power can be overload protected by dual (two line) fuses.

Figure 10:
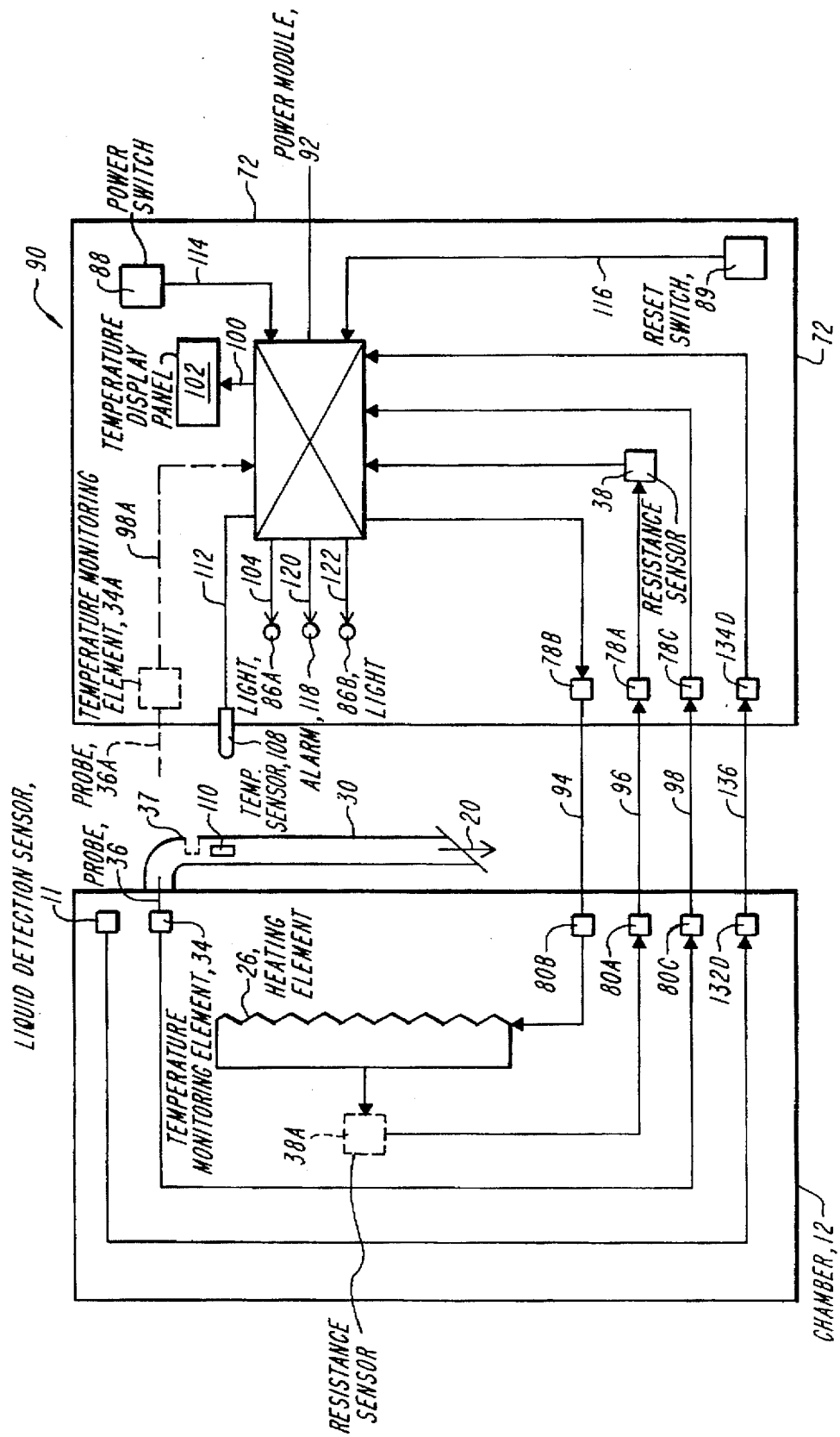
FIG. 10 shows the internal circuit loop for the system of the present invention for monitoring and controlling temperature and power equipped with an infrared temperature sensor.

The internal circuit loop 90 for controlling temperature and power is shown in FIG. 10. The controller 72 supplies power from the power module 92 via electrical line 94 through electrical connection pads 80B and 78B to the heating element 26. The resistance of heating element 26 can be monitored via line 96 through electrical connection pads 80A and 78A by a resistance sensor 38 which can be disposed on the controller 72. Alternatively, a resistance sensor 38A (shown in dotted lines in FIG. 10) can be located on the chamber 12. In addition, if the alloy which makes up the conductor of the heating element 26 has a large temperature coefficient of resistance, the electrical resistance of the heating element 26 itself can be used to measure the temperature of the heating element and correlated to fluid temperature. Using this method, an upper limit on the resistance of the heating element 26 can be used as an over temperature sensor for the fluid. The probe 36 of the temperature monitoring element 34 can be disposed in the outlet port 30 to monitor the temperature of the fluid 20 exiting the chamber 12. This information is transmitted back to the power module 92 via line 98 through electrical connection pads 80C and 78C. Alternatively, the temperature monitoring element 34A (shown in dotted lines in FIG. 10) can be disposed on the controller and its probe 36A can be inserted into a sleeve 37 or other portion of the outlet port 30 of the chamber 12. This information can be transmitted back to the power module 92 via line 98A. The actual temperature of the fluid can then be relayed via line 100 to the temperature display panel 102 and/or relayed via line 104 to at least one light 86A indicating whether the temperature has reached the desired level. Additional temperature monitoring and control can be accomplished with an infrared temperature sensor 108 disposed on the controller 72 which senses outlet fluid temperature through a window 110 on the chamber outlet port 30 or elsewhere in the fluid line. This information can be relayed to the power module 92 via line 112 and also used for the temperature monitoring. A liquid detection sensor 11 can be employed to measure resistance of the fluid in the tube. If sensor 11 detects a lack of fluid (e.g., a high resistance) a shut-off signal can be relayed via line 136 and electrical connection pads 132 D and 134 D to the power module 92. The power ON/OFF switch 88 can be relayed to the power module 92 via line 114. The RESET switch 89 can be relayed to the power module 92 via line 116.

If the resistance or temperature exceeds a pre-determined level, the power module 92 can automatically shut off power to the heating element 26. In addition, the power module can sound an alarm 118 via line 120 and/or illuminate a warning light 86B via line 122 to warn the user of a fault condition.

In sum, the present invention benefits from the recognition that an electrically resistive heating element can be molded into a flow-through chamber, and this chamber can be inserted in a flow-line for warming fluids to normothermic temperatures prior to the delivery of such fluids to a body. Further, the devices and methods of the present invention have several advantages over the traditional devices and techniques for heating such fluids. The incorporation of the heating element inside the polymeric, flow-through chamber provides that device can be inserted in one simple step directly in the fluid delivery line. In contrast, the traditional techniques may require multiple steps such as placing a bag or conduit of fluid inside an enclosure, pressing or clamping heating plates against the fluid container, and subsequently, removing the heating plates prior to fluid delivery.

In addition, in comparison with the traditional techniques for warming delivery fluids, the devices and methods of the present invention provide unique and accurate temperature monitoring and control. For example, the device can employ a probe of a temperature monitoring element inserted directly in the flow line of the fluid exiting the chamber. Alternatively or additionally, the device can employ an infrared sensor for sensing the outlet fluid temperature through window molded in the exit port of the chamber. In contrast, the traditional techniques typically only monitor the temperature of the heating plate and/or fluid container.

It will be understood that the above description pertains to only several embodiments of the present invention. That is, the description is provided above by way of illustration and not by way of limitation. For example, other chamber shapes, flow paths, resistance and temperature monitoring and control configurations can be selected consistent with the present invention. The invention is further characterized according to the following claims.

What is claimed is:

1. A fluid heating apparatus for warming an infusion or irrigation liquid prior to delivery of the liquid to a patient, the apparatus comprising:

a flow-through polymeric chamber through which the liquid flows, the polymeric flow-through chamber having a fluid inlet port and a fluid outlet port;

at least one electrically resistive heating element disposed in a wall of the chamber for heating the liquid, the heating element having a surface area of at least about 15 cm$^2$; and an electrical connection element for connecting the heating element to a controller for power and temperature control.

2. The apparatus of claim 1, further comprising:
a temperature monitoring element disposed within the chamber for measuring an outlet temperature of the liquid exiting the chamber.

3. The apparatus of claim 2 wherein the temperature monitoring element comprises a probe disposed in an outlet flow path of the liquid exiting the chamber.

4. The apparatus of claim 3 wherein the temperature monitoring element comprises a thermistor.

5. The apparatus of claim 1 wherein the at least one heating element comprises a heating element selected from the group consisting of:
an etched metal foil,
a carbon dispersion resistor, and
a dye-cut resistor.

6. The apparatus of claim 1 wherein the apparatus further comprises a sensor disposed within the chamber for detecting the absence of liquid in the chamber.

7. The apparatus of claim 1 wherein the apparatus is disposable.

8. The apparatus of claim 1 wherein the chamber has first and second side walls and a center wall disposed therebetween, and the at least one heating element is embedded in the center wall.

9. The apparatus of claim 1 wherein the apparatus further comprises a biocompatible protective material disposed between a surface of the at least one heating element and the inside of the chamber.

10. The apparatus of claim 1 wherein the apparatus further comprises an insulating material disposed to surround at least a portion of an outer surface of the chamber to reduce heat losses.

11. The apparatus of claim 9, wherein the heating element is contained between two layers of polyimide.

12. The apparatus of claim 1 wherein the apparatus further comprises baffles disposed within the chamber for forming a restricted labyrinth flow path.

13. The apparatus of claim 1 wherein the at least one heating element has a capacity for emitting at least about 50 Watts.

14. The apparatus of claim 1 wherein the apparatus has a capacity for a fluid flow ranging from about 10 ml/min to about 1000 ml/min.

15. A fluid heating system for warming an infusion or irrigation liquid prior to delivery of the liquid to a patient, the system comprising:
a flow-through polymeric chamber through which the liquid flows, the polymeric flow-through chamber having a fluid inlet port and a fluid outlet port;
at least one electrically resistive heating element disposed in a wall of the chamber for heating the liquid, the heating element having a surface area of at least about 15 cm$^2$; and an external controller in electrical connection with the heating element for controlling the power to the heating element.

16. The system of claim 15 wherein the controller comprises a LED display for indicating a two-digit temperature display of an outlet liquid temperature and at least one light for indicating when the outlet liquid temperature is within a pre-determined temperature range.

17. The system of claim 15, further comprising:
an attachment mechanism for attaching the controller to the chamber to receive an electrical connection element disposed on the chamber.

18. The system of claim 16, further comprising:
a resistance sensor integrated into the chamber for sensing an electrical resistance of the at least one heating element.

19. The system of claim 15 wherein the system further comprises a power shut-off circuit loop for automatically shutting off power to the at least one heating element when a fault condition occurs.

20. The system of claim 15 wherein the system further comprises an alarm in electrical connection with and responsive to the controller for sounding when a fault condition occurs.

21. The system of claim 15 wherein the system further comprises a mounting mechanism on the controller for mounting the controller to a support pole.

22. The system of claim 15 wherein the system further comprises an infrared temperature sensor disposed on the controller for sensing the outlet liquid temperature.

23. A method for warming an infusion or irrigation fluid entering a biological body, the method comprising the steps of:
providing a polymeric flow-through chamber through which the fluid may pass, the polymeric flow-through chamber having a fluid inlet port and a fluid outlet port;
providing at least one electrically resistive heating element that is disposed in a wall of the chamber for heating the liquid, the heating element having a surface area of at least about 15 cm$^2$;
flowing the fluid though the chamber; and
heating the fluid with the at least one heating element while the fluid passes through the chamber.

24. The method of claim 23 wherein the heating step further comprises heating the fluid to a desired predetermined temperature range of about 34° C. to about 45° C.

25. The method of claim 24 wherein the heating step further comprises heating the fluid to a maximum of about 50° C. above a storage temperature of the fluid.

26. The method of claim 24, further comprising the step of:
monitoring the temperature of the at least one heating element by measuring the resistance across the heating element and correlating the resistance to the temperature of the heating element.

* * * * *